United States Patent

Kuroda et al.

[11] 4,143,135
[45] Mar. 6, 1979

[54] ANTIBIOTIC PHOSPHONIC ACID DERIVATIVES AND PRODUCTION AND USE THEREOF

[75] Inventors: Yoshio Kuroda, Osaka; Masakuni Okuhara, Ikeda; Eiko Iguchi, Osaka; Hatsuo Aoki, Ikeda; Hiroshi Imanaka, Mishima, all of Japan

[73] Assignee: Fujisawa Pharmaceutical Co., Ltd., Osaka, Japan

[21] Appl. No.: 819,551

[22] Filed: Jul. 27, 1977

[30] Foreign Application Priority Data

Jul. 27, 1976 [GB] United Kingdom ............... 31339/76

[51] Int. Cl.$^2$ .................... A61R 31/16; A61R 31/165; C07F 9/38
[52] U.S. Cl. ..................................... 424/211; 195/42; 260/502.5
[58] Field of Search ...................... 260/502.5; 424/217

[56] References Cited

U.S. PATENT DOCUMENTS

| | | | |
|---|---|---|---|
| 2,381,071 | 8/1945 | McNally et al. | 260/502.5 |
| 2,993,067 | 7/1961 | Magerlein et al. | 260/502.5 |
| 3,812,221 | 5/1974 | Braden et al. | 260/502.5 |
| 3,832,394 | 8/1974 | Niida et al. | 260/502.5 |
| 3,970,586 | 7/1976 | Schliebs et al. | 260/502.5 |

*Primary Examiner*—Joseph E. Evans
*Attorney, Agent, or Firm*—Oblon, Fisher, Spivak, McClelland & Maier

[57] ABSTRACT

An antibiotic FR-900098 which has been assigned the chemical structure

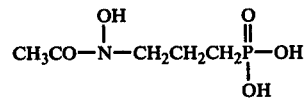

and another antibiotic FR-33289 which has been assigned the chemical structure

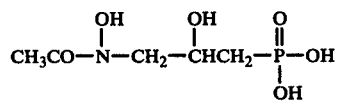

have been isolated from cultured broths.

9 Claims, No Drawings

ANTIBIOTIC PHOSPHONIC ACID DERIVATIVES AND PRODUCTION AND USE THEREOF

BACKGROUND OF THE INVENTION

This invention relates to novel antibiotics, phosphonic acid derivatives which have antimicrobial activities against various pathogenic bacteria, to processes for production thereof, and to pharmaceutical compositions comprising the same.

The inventors of this invention first and originally isolated a new antibiotic, hereinafter called the antibiotic FR-900098, in pure form from a cultured broth obtained by fermentation of a strain of genus Streptomyces, identified the same by the physico-chemical properties and also discovered the utility thereof, namely that said antibiotic FR-900098 has antimicrobial activities against various pathogenic microorganisms.

After the first isolation of the antibiotic FR-900098, said antibiotic FR-900098 was delivered to the chemists (i.e. the inventors of U.S. application Ser. No. 819,554 filed on the same date as the filing date of this application) of the Synthesis section of the Research Laboratory of Fujisawa Pharmaceutical Co., Ltd., Japan to which the inventors of this invention also belonged, for identification of its chemical structure. Then, said chemists succeeded in identifying the chemical structure and assigned the chemical structure to the antibiotic FR-900098 as follows.

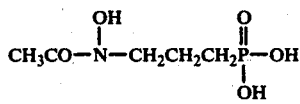

[3-(N-acetyl-N-hydroxyamino)propylphosphonic acid]
Further, the inventors of this invention first and originally isolated another antibiotic, hereinafter called the antibiotic FR-33289 from a cultured broth obtained by fermentation of a strain of genus Streptomyces, identified the same by the physico-chemical properties and the chemical structure which is assigned as follows, and discovered the utility thereof, namely that said antibiotic FR-33289 has antimicrobial activities against various pathogenic microorganisms.

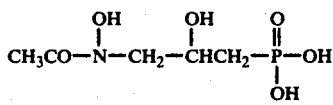

[3-(N-acetyl-N-hydroxyamino)-2-hydroxypropylphosphonic acid]

With regard to the novel antibiotics mentioned above, it is to be noted that the chemists indicated above made extensive studies on synthetic methods for preparing the same and succeeded in devising synthetic methods for preparing the antibiotic FR-900098 as well as the antibiotic FR-33289, including various derivatives thereof, which was filed as a U.S. patent application under the Ser. No. 819,554 on the same date as the filing date of this U.S. patent application.

DETAILED DESCRIPTION OF THE PREFERRED EMBODIMENTS OF THE INVENTION

This invention relates to novel antibiotics which have antimicrobial activities against various pathogenic microorganisms. More particularly, it relates to novel antibiotics FR-900098 and FR-33289, to processes for the production thereof, to pharmaceutical compositions comprising the same and to a method of use of the same for the therapeutical treatment of infectious disease in human beings and animals.

Accordingly, it is an object of this invention to provide novel antibiotics FR-900098 and FR-33289 which are active against various pathogenic microorganisms.

Another object of this invention is to provide processes for production of the same by culturing a stain belonging to the genus Streptomyces in a nutrient medium.

A further object of this invention is to provide a pharmaceutical composition comprising the same.

Novel antibiotic phosphonic acid derivatives of this invention, i.e., FR-900098 and FR-33289 can be represented by the following formula (I):

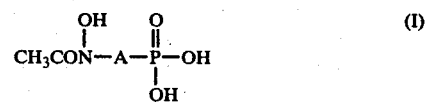

wherein A is trimethylene (—CH$_2$CH$_2$CH$_2$—) or 2-hydroxytrimethylene

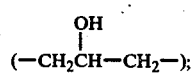

In this respect, it is to be noted that the antibiotic FR-900098 is the compound represented by formula (I) wherein A is trimethylene and the antibiotic FR-33289 is the compound (I) whereinA is 2-hydroxytrimethylene.

The antibiotics FR-900098 and FR-33289 of this invention are produced by culturing a micro-organism belonging to the genus Streptomyces in a conventional manner. Particularly, the said antibiolics are produced by culturing a microorganism belonging to the genus Streptomyces such as *Streptomyces rubellomurinus*, *Streptomyces rebellomurinus* subsp. *indigoferus* and the like. More particularly, the antibiotic FR-900098, i.e., the compound [I] wherein A is trimethylene is produced by fermentation of *Streptomyces rubellomurinus* and subspecies *indigoferus* thereof and the antibiotic FR-33289, i.e., the compound [I] wherein A is 2-hydroxytrimethylene, is produced by fermentation of *Streptomyces rubellomurinus* subsp. *indigoferus*.

The fermentation of said microorganisms is conducted in a nutrient medium containing assimilable sources of carbon and nitrogen, preferably under aerobic conditions (e.g., shaking culture, submerged culture, etc.), the details of which will be apparent in the following.

The preferred sources of carbon in the nutrient medium are carbohydrates such as glucose, fructose, glycerin and starch. Other sources which may be included are lactose, arabinose, xylose, dextrin, molasses and the like.

The preferred sources of nitrogen are yeast extract, peptone, gluten meal, cottonseed meal, soybean meal, corn steep liquor, dried yeast, wheat germ, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials, which contain traces of growth factors and considerable quantities of mineral nutrients, are also suitable for use. When desired, there may be added to the medium mineral salts such as calcium carbonate, sodium or potassium phosphate, sodium or potassium chloride, magnesium salts, copper salts and the like. If necessary, especially when the culture medium foams seriously, a defoaming agent, such as liquid paraffin, fatty oil, plant oil, mineral oil or silicone may be added.

As is the case of the preferred methods used for the production of other antibiotics in massive amounts, submerged aerobic cultural conditions are preferred for the production of the antibiotics in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the antibiotics. Accordingly, it is desirable first to produce a vegetative inoculum of the organism by inoculating a relatively small quantity of culture medium with spores of mycelia of the organism and culture them and to transfer the cultured vegetative inoculum aseptically to large tanks. The medium in which the vegetative inoculum is produced can be substantially the same as or different from the medium utilized for the production of the antibiotics.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 30° C., for a period of 50 hours to 100 hours.

The antibiotics can be recovered from the culture medium by conventional means which are commonly used for the recovery of other known antibiotics.

In general, most of the antibiotics produced are found in the cultured broth, and accordingly the antibiotics can be separated from the filtrate, which is obtained by filtering or centrifuging the broth, by a conventional method such as concentration under reduced pressure, lyophilization, extraction with solvent, pH adjustment, treatment with a resin (e.g., anion or cation exchange resin, non-ionic adsorption resin), treatment with an adsorbent (e.g., activated charcoal, silicic acid, silica gel, cellulose, alumina), crystallization, recrystallization and the like.

(I). Production of the antibiotic FR-900098, i.e., the compound (I) wherein A is —$CH_2$—$CH_2$—$CH_2$—, i.e., 3-(N-acetyl-N-hydroxyamino)propylphosphonic acid:

The antibiotic FR-900098 can be produced by fermentation of an antibiotic FR-900098-producing strain belonging to genus Streptomyces such as *Streptomyces rubellomurinus* and *Streptomyces rubellomurinus* subsp. *indigoferus* in a nutrient medium.

(1) The microorganisms:

The microorganisms which can be used for the production of the new antibiotic FR-900098 are strains of *Streptomyces rubellomurinus* newly isolated from a soil sample collected at Mt. Hira, Siga Prefecture, Japan, and of *Streptomyces rubellomurinius* subsp. *indigoferus* newly isolated from a soil sample collected at Koganei city, Tokyo, Japan.

A culture of the living organism of *Streptomyces rubellomurinus* has been deposited with and added to a permanent stock culture collection of the American Type Culture Collection, under ATCC No. 31215. Further, a culture of the organism has been deposited with Fermentation Research Institute, Agency of Industrial Science and Technology, Japan, under the receipt No. 3563.

A culture of the living organism of *Streptomyces rubellomurinus* subsp. *indigoferus* has been deposited with and added to a permanent stock culture collection of the American Type Culture Collection, under ATCC No. 31304. Further, a culture of the organism has been deposited with Fermentation Research Institute, Agency of Industrial Science and Technology, Japan.

It is to be understood that the production of the new antibiotic is not limited to the use of the particular organism described herein, which is given only for illustrative purposes. That is, an artificial mutant as well as the natural strain can also be used for the production the antibiotic. Such an artificial mutant is produced from the organism described herein by conventional means, such as X-rays, ultra-violet radiation, N-methyl-N'-nitro-N-nitrosoguanidine, 2-amino-purine and nitrogen mustard oils.

(1) Microbiological Properties (1)-1 *Streptomyces rubellomurinus* ATCC 31215:

*Streptomyces rubellomurinus* ATCC 31215 has the following morphological, cultural and physiological characteristics:

1. Morphological characteristics:

The morphology of the culture was microscopically observed with the mycelium grown on each of sucrose-nitrate, agar, glycerol-asparagine agar, yeast-melt extract agar and oatmeal agar, at 30° C. for 10-14 days.

(1) Type of branching of spore-forming hyphae:
  Monopodial branching
(2) Form of spore-forming hyphae:
  Straight or Curved (Rectiflexibiles)
(3) Number of spores:
  10–50 spores
(4) Surface appearance and size of spores:
  Smooth, 0.4–0.8 × 1.1–1.6 micron
(5) Existence of zoospore:
  Not observed
(6) Existence of sporangium:
  Not observed
(7) Formation of spores:
  At aerial mycelium 2. Cultural characteristics:

The strain has the following cultural characteristics when grown on media as indicated below at 30° C. for 10–14 days.

| Medium | Aerial mycelium | Vegetative growth | Soluble pigment |
|---|---|---|---|
| (1) Sucrose-nitrate agar | very thin, white | colorless, small colonies | none |

-continued

| | Medium | Aerial mycelium | Vegetative growth | Soluble pigment |
|---|---|---|---|---|
| (2) | Glucose-asparagine agar | pinkish gray, short cottony | pale yellow, small colonies | none or trace |
| (3) | Glycerol-asparagine agar | none | scant growth | none |
| (4) | Starch-inorganic salts agar | gray-pinkish gray, short cottony | pale yellow, colonies | none |
| (5) | Tyrosine agar | none | scant growth | none |
| (6) | Nutrient agar | none | scant growth | none |
| (7) | Yeast-malt extract agar | white-pink, short cottony | pale yellow, small colonies | none |
| (8) | Oatmeal agar | pinkish gray, short cottony | pale yellow, small collonies | none |
| (9) | Glucose-peptone gelatin stab* | white-pink, short cottony | colorless | none |
| (10) | Milk | faint growth on surface | pale yellow | none or trace |
| (11) | Peptone-yeast iron agar | none | scant growth | none |

*at ambient temperature for 20 days

3. Physiological characteristics:
  (1) Range of temperature for growth (on Bennett's agar slants): 12–40° C., optimum: 27° C.
  (2) Liquefaction of gelatin (on glucose - peptone gelatin stab): negative
  (3) Hydrolysis of starch (on starch - inorganic salts agar): positive
  (4) Coagulation and peptonization of skim milk:
    Coagulation: positive
    Peptonization: weak
  (5) Production of melanoid pigment (on tyrosine agar, peptone — yeast iron agar and tryptone — yeast extract broth): negative
  (6) Cell-wall pattern:
    I type (containing LL-diaminopimelic acid)
  (7) Carbon source utilization patterns (on Pridham-Gottlieb agar)

| Carbon source | Growth |
|---|---|
| L-Arabinose | ++ |
| D-Xylose | + |
| D-Glucose | ++ |
| D-Fructose | + |
| Sucrose | ± |
| Inositol | − |
| L-Rhamnose | − |
| Raffinose | ± |

As a result of looking up the strains possessing the characteristics mentioned above by referring to the literature, namely, "Bergey's Manual of Determinative Bacteriology" eighth edition (1975), "The Actinomycetes" Vol. II (1961) written by S. A. Waksman and "The International Streptomyces Project Reports" written by E. B. Shirling and D. Gottlieb {Cf. International Journal of Systematic Bacteriology Vol. 18, pages 69 and 279 (1968), Vol. 19, page 391 (1969) and Vol. 22, page 265 (1972)}, Streptomyces sindenensis, Streptomyces xanthocidicus and Streptomyces exfoliatus have been detected as species having relatively analogous characteristics to those of the strain ATCC No. 31215.

The strain ATCC No. 31215, however, is different from these analogous species in the following respects.
(i) *Streptomyces sindenensis:*

Mature spore chains of *Streptomyces sindenensis* are generally short. Spores of the species are poor on starch-inorganic salts agar. Aerial mycelia of the species are slightly formed on glycerol-asparagine agar. A strain of the species can assimilate D-mannitol.

(ii) *Streptomyces xanthocidicus:*

Aerial mycelia of *Streptomyces xanthocidicus* are abundant on both glycerol-asparagine agar and yeast-malt extract agar. Some strains of the species produce melanoid pigments. A strain of the species can relatively strongly assimilate sucrose and raffinose.

(iii) *Streptomyces exfoliatus*

Aerial mycelia of *Streptomyces exfoliatus* are formed on glycerol-asparagine agar. Spores of the species are very abundant on yeast-malt extract agar. A strain of the species can relatively strongly assimilate sucrose and raffinose. Neither fragmentation nor spore formation of the species on substrate mycelium are observed.

In view of the result of the above observation and in view of the fact that the strain ATCC 31215 is capable of producing the new antibiotic FR-900098, the strain ATCC 31215 can be judged to be a new species belonging to the genus *Streptomyces* and this has been designated as Streptomyces rubellomurinus.

(1)-2 *Streptomyces rubellomurinus* subsp. *indigoferus* ATCC 31304:

*Streptomyces rubellomurinus* subsp. *indigoferus* ATCC 31304 has the following morphological, cultural and physiological characteristics:

1. Morphological characteristics:
    Microscopic observations were made on cultures which were grown at 27° C. for from 10 to 14 days on sucrose-nitrate agar, glycerin-asparagine agar, yeast-malt extract agar, oatmeal agar, and inorganic salts-starch agar.
    (1) Sporophore morphology: monopodial branching, rectiflexibles
      Spore chains are generally long, with more than 10 spores per chain.
    (2) Spore surface: smooth
    (3) Spore size: 0.4–0.9 × 1.0–1.6 micron
    (4) Neither fragmentation of hyphae nor formation of spores occur in the substrate mycelium. Sporangium and zoospore are not observed.

2. Cultural characteristics:
    The strain has the following cultural characteristics when grown on media as indicated below at 27° C. for 10 days.

|     | Medium | Aerial mycelium | Vegetative growth | Soluble pigment |
| --- | --- | --- | --- | --- |
| (1) | Sucrose-nitrate agar | white gray, to very thin powdery | colorless, small colonies | none |
| (2) | Glucose-asparagine agar | pinkish gray, short cottony | pale yellow, small colonies | none or trace of yellow |
| (3) | Glycerin-asparagine agar | none | scant growth | none |
| (4) | Starch-inorganic salts agar | mouse gray to pinkish gray, short cottony | Pale yellow to pale yellowish brown, small colonies | none or trace of yellow |
| (5) | Tyrosine agar | none | scant growth | none |
| (6) | Nurient agar | none | scant growth | none |
| (7) | Yeast-malt extract agar | white, thin powdery | pale yellow to pale yellowish brown, wrinkled margin, indigo color | none |
| (8) | Oatmeal agar | Pinkish gray, short cottony | pale yellow, small colonies | none |
| (9) | Bennett's agar | white to pinkish gray, powdery | pale yellow to slightly indigo color, small colonies | none |
| (10) | Glucose-peptone gelatin stab. | white to pink, short cottony | colorless, faint growth | none |
| (11) | Peptone-yeast iron agar | none | colorless to slightly indigo color, faint growth | none |
| (12) | Milk | white, very thin powdery | pale yellow, growth on surface ring | none or trace |

3. Physiological properties:
  (1) Range of temperature for growth (on Bennett's agar slants):
    12°–40° C., optimum: 27° C.
  (2) Liquefaction of gelatin (on glucose-peptone gelatin stab):
    negative
  (3) Hydrolysis of starch (on starch-inorganic salts agar):
    strongly hydrolyzed
  (4) Coagulation and peptonization of skim milk:
    Coagulation followed weak peptonization
  (5) Production of melanoid pigment (on tyrosine agar, peptone-yeast iron agar and tryptone-yeast extract broth):
    negative
  (6) Carbon source utilization patterns (on Pridham-Gottlieb agar):

| Carbon source | Growth |
| --- | --- |
| L-arabinose | ++ |
| cellulose | − |
| D-fructose | + |
| D-galactose | + |
| D-glucose | + |
| glycerin | + |
| inositol | − |
| lactose | − |
| D-maltose | + |
| D-mannitol | − |
| D-mannose | − |
| raffinose | − |
| L-rhamnose | − |
| salicin | − |
| Starch | + |
| sucrose | − |
| D-xylose | + |

Symbols: +, positive utilization; −, no utilization

The above microscopic and cultural studies indicate that the strain ATCC 31304 belongs to the genus Streptomyces. Accordingly, a comparison of this organism was made with the published descriptions of Streptomyces species. From the above-mentioned information, the strain ATCC 31304 is considered to closely resemble *Streptomyces rubellomurinus* ATCC 31215. It was found, however, that this species was differentiated from the strain ATCC 31304 in the indigo color of vegetative mycelium on media containing yeast extract. As a result of the comparisons, the strain ATCC 31304 is considered as subspecies of *Streptomyces rubellomurinus*, and the name Streptomyces rubellomurinus subsp. *indigoferus* is assigned.

(2) Fermentation

Fermentation for production of the antibiotic FR-900098 can be conducted by conventional means as mentioned hereinabove, and isolation of the antibiotic FR-900098 can also be conducted by conventional means as mentioned hereinabove.

However, as mentioned hereinafter, when *Streptomyces rubellomurinus* subsp. *indigoferus* is used for production of the antibiotic FR-900098, the antibiotic FR-33289 as well as FR-900098 is simultaneously produced in the cultured broth.

Accordingly, these two antibiotics may be separated in a conventional manner such as by chromatography. The following is mentioned as one example of the separation method.

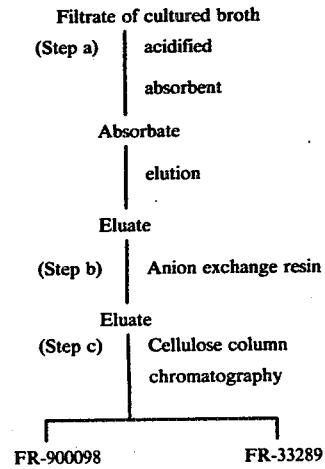

Step a:

The filtrate is acidified in a conventional manner, e.g., adjusted to pH 2.8 and the solution is passed through a column of an appropriate absorbent such as charcoal. Elution is carried out with an aqueous solvent (e.g., methanol, acetone, etc.).

Step b:

The eluate is passed through a column of an anion exchange resin (e.g., DEAE-Sephadex, Duolite A-6, etc.). Elution is carried out with, for example, aqueous sodium chloride (e.g. 0.3 N), aqueous ammonia (e.g. 0.2 M) and the like. The above operations (Step a and b) are advantageously repeated several times.

Step c:

The eluate is subjected to column chromatography using cellulose with a suitable developing solvent (e.g., aqueous propanol, etc.). The antibiotic FR-900098 can be separated, for example, by developing with 75% aqueous propanol, and FR-33289 can be separated by developing with 70% aqueous propanol.

(3) The antibiotic FR-900098:

The antibiotic FR-900098 as obtained according to the aforementioned process, has as its monosodium salt, the following physical and chemical properties:

(a) Elemental Analysis (%): C27.74; H5.03; N6.66 (the others: phosphorus and oxygen)

(b) MP: 193°–194° C.

(c) Specific rotation: $[\alpha]_D^{25} = 0$ (C=1.0, in water)

(d) Ultraviolet absorption spectrum: $\lambda_{max}^{H_2O}$ or $_{0.1NHCl}$ = end absorption; $\lambda_{max}^{0.1N\ NaOH}$ = 230 nm (Shoulder) ($E_1^{1\%}$ cm = 325)

(e) Infrared absorption spectrum: $\nu_{max}^{KBr}$ = 3450, 3400, 3350, 3100, 2930, 2800, 2420, 2320, 1615, 1570, 1495, 1450, 1420, 1370, 1310, 1280, 1240, 1220, 1200, 1180, 1160, 1090, 1080, 1050, 1040, 990, 980, 925, 910, 885, 810, 780, 760, 740, 710 cm$^{-1}$.

(f) Solubility:
Very soluble; water, methanol.
Sparingly soluble; acetone, propanol.
Insoluble; ethyl acetate, chloroform, benzene, (g) Color reactions:
Positive; each reaction with ferric chloride, potassium permanganate and iodine vapor.
Negative; ninhydrin reaction and Molish's reaction.

(h) Form and color of crystals:
Colorless prisms (recrystallized from a mixture of methanol and acetone)

(i) Thin layer chromatography:
Stationary phase; Eastman chromatogram Sheet Cellulose No. 13254 (trade name, made by Eastman Kodak Co.)

| Developing solvent | Rf value |
|---|---|
| 75% Aqueous propanol | 0.5 |
| n-Butanol saturated with water | 0 |
| 70% Aqueous acetonitrile | 0.4 |

From the analysis of the above physical and chemical properties and the results of further investigations for identification of chemical structure by the chemists as indicated hereinabove, the chemical structure of the antibiotic FR-900098 has been identified and assigned as follows.

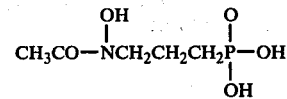

[3-(N-acetyl-N-hydroxyamino)propylphosphonoic acid]

(II). Production of the antibiotic FR-33289, i.e., the compound (I) wherein A is

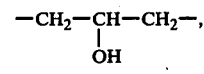

i.e., 3-(N-acetyl-N-hydroxyamino)-2-hydroxypropyl-phosphonic acid:

The antibiotic FR-33289 can be produced by fermentation of an antibiotic FR-33289-producing strain belonging to genus Streptomyces such as *Streptomyces rebellomurinus* subsp. *indigoferus* in a nutrient medium.

(1) The microorganism:

A preferred microorganism which can be used for the production of the new antibiotic FR-33289, is *Streptomyces rubellomurinus* subsp. *indigoferus* ATCC 31304.

Microbiological properties of the strain ATCC 31304 are described hereinabove.

Further, it is to be noted that *Streptomyces rubellomurinus* subsp. *indigoferus* ATCC 31304 can produce simultaneously both the antibiotic FR-900098 and the antibiotic FR-33289 in a broth cultured as mentioned hereinabove.

(2) The fermentation:

Fermentation for production of the antibiotic FR-33289 can be conducted by conventional means as mentioned hereinabove, and isolation of the antibiotic can generally also be conducted by conventional means as mentioned hereinabove.

As mentioned above, the cultured broth contains both the antibiotic FR-900098 and the antibiotic FR-33289 and accordingly these two antibiotics may be separated.

Preferred separation operations are the same as mentioned above.

(3) The antibiotic FR-33289:

The antibiotic FR-33289 as obtained according to the afore-mentioned process, has, in the form of its monosodium salt, the following physical and chemical properties:

(a) Infra-red absorption spectrum: $\nu_{max}^{KBr}$ = 3300, 2900, 2400, 1740, 1620, 1420, 1240, 1140, 1040, 900 cm$^{-1}$.

(b) N.M.R. Spectrum: δ(ppm) in D$_2$O 1.88 (2H, d.d. J=6 and 18Hz), 2.16 (3H, s), 3.66–3.9 (2H, m), 4.30 (1H, m).

(c) Color reactions:
Positive: reaction with ferric chloride, potassium permanganate, and iodine vapor.

(d) Thin layer chromatography: Stationary phase; Eastman chromatogram Sheet Cellulose No. 13254 (trade name, made by Eastman Kodak Co.)

| Eastman Kodak Co. | |
|---|---|
| Developing Solvent | R$_f$ |
| 60% Aqueous propanol | 0.6 |

From the analysis of the above and the chemical properties and as a result of further investigation by the inventor of this invention for identification of chemical structure, the chemical structure of the antibiotic FR-33289 has been identified and assigned as follows.

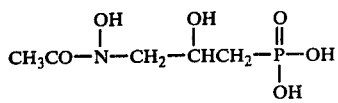

[3-(N-acetyl-N-hydroxyamino)-2-hydroxypropylphosphonic acid]

The antibiotics FR-900098 and FR-33289 thus produced in the culture broth can be isolated in the free form, i.e., FR-900098 per se and FR-33289 per se and when the solution or concentrate containing the antibiotics FR-900098 and/or FR-33289 is treated with an inorganic base such as an alkali metal compound (e.g., sodium hydroxide, potassium hydroxide, etc.), alkaline earth metal compound (e.g., calcium hydroxide, magnesium hydroxide, etc.), ammonia or the like; with an organic base (e.g. ethanolamine, triethylamine, dicyclohexylamine, N,N'-dibenzylethylenediamine, etc.); or with an amino acid (e.g., arginine, aspartic acid, glutamic acid, etc.), during the processes, e.g., extraction, isolation, or purification processes, the antibiotics FR-900098 and FR-33289 may be isolated in the form of the corresponding salts thereof.

Further, the antibiotics FR-900098 and FR-33289 obtained in their free form may also be converted to the corresponding salt thereof with a base such as an inorganic base or an organic base as mentioned above or an amino acid in a conventional manner. Alternatively, such salts of the antibiotics FR-900098 and FR-33289 may be easily converted to the free form by treatment with an acid such as a mineral acid (e.g., hydrochloric acid, etc.) in a conventional manner.

Accordingly, it is to be understood that this invention includes within the scope thereof the antibiotics FR-900098 and FR-33289 as well as the salts thereof that is salts with organic or inorganic bases (e.g., sodium salt, potassium salt, calcium salt, magnesium salt, ammonium salt, triethylamine salt, ethanolamine salt, dicyclohexylamine salt, ethylenediamine salt, N,N'-dibenzylethylenediamine salt, etc.) or salts with amino acids (e.g., arginine salt, aspartic acid salt, glutamic acid salt, etc.) and the like.

Biological Properties of Hydroxyaminohydrocarbonphosphonic Acid Derivatives

Antimicrobial activity:

The object compounds, FR-900098 and FR-33289, and the pharmaceutically acceptable salts thereof, have been found to possess strong antibacterial activity against pathogenic microorganisms such as Gram positive and negative bacteria, including the genera Bacillus, Sarcina, Escherichia, Proteus, Salmonella, Pseudomonas, Shigella and Enterobacter.

Accordingly, the object compounds of this invention are useful for the treatment of infectious disease caused by such pathogenic bacteria in human beings or animals. For illustrative purposes, the biological properties of the antibiotic FR-900098, as a representative compound of the invention, is illustrated in the following.

1. Monosodium salt of 3-(N-acetyl-N-hydroxyamino)-propylphosphonic acid (FR-900098):

Minimum Inhibitory Concentration (M.I.C.):

M.I.C. test was conducted by the usual serial agar dilution method, using a nutrient agar which was incubated at 37° C. for 20 hours. M.I.C. value is expressed as the minimum concentration of the monosodium salt of 3-(N-acetyl-N-hydroxyamino)propylphosphonic acid (mcg/ml.) which inhibits growth of the microorganism. The results are as follows:

| Test Microorganisms | M.I.C. (mcg/ml.) |
|---|---|
| Staphylococcus aureus FDA209P JC-1 | > 1000 |
| Bacillus subtilis ATCC6633 | 125 |
| Sarcina lutea PCI1001 | 8 |
| Escherichia coli NIHJ JC-2 | 63 |
| Escherichia coli 1341-29 | 32 |
| Klebsiella pneumoniae NCTC 418 | 500 |
| Proteus vulgaris IAM 1025 | 125 |
| Proteus mirabilis 1 | > 1000 |
| Proteus morganii 30 | > 1000 |
| Proteus rettgeri 15 | 63 |
| Pseudomonas aeruginosa IAM 1095 | 250 |
| Salmonella typhi T-287 | 2 |
| Shigella flexneri IaEW8 | 8 |
| Serratia marcescens 5 | 250 |
| Citrobacter freundii 20 | 500 |
| Enterobacter aerogenes 10 | 32 |
| Enterobacter cloacae 25 | 63 |

Protecting Effect in Experimental Mice Infections:

The activity of the monosodium salt of 3-(N-acetyl-N-hydroxyamino)propylphosphonic acid in vivo against the species Escherichia coli was tested, using ICR-strain male mice weighing 20-25g. Two groups, each of four mice, were fasted for 24 hours prior to the testing.

A suspension of a pathogenic bacteria, Escherichia coli strain No. 1341-29 in 2.5% aqueous Mucin solution (0.5 ml.) was intraperitoneally injected into each mouse (Challenge Dose: 1 × 10$^6$ living cells/mouse), one group being used for testing the projecting effect and the other for control.

One hour after the infection, each mouse of the experimental group was subcutaneously injected with the monosodium salt of 3-(N-acetyl-N-hydroxyamino)-propylphosphonic acid (4 mg.) in water (0.5 ml.), the mice of the control group net being treated with the antibiotic.

Animals in both of the groups were observed for death and survival for 1 week.

All mice of the experimental group survived. On the other hand, all mice of the control group died.

Acute Toxicity:

A solution of the monosodium salt of 3-(N-acetyl-N-hydroxyamino)propylphosphonic acid in water (0.5 ml.) was intravenously injected into each of five mice (Dose : 5g/kg mouse). All the mice normal for 10 days after administration.

The Pharmaceutical Composition

The object compound (I), i.e., the antibiotics FR-900098 and FR-33289 and the pharmaceutically acceptable salts thereof can be formulated for administration in any convenient way, analogously with known antibiotics, in admixture with a non-toxic pharmaceutically acceptable carrier.

A pharmaceutically acceptable salt of the compound (I) may include a salt with an inorganic or organic base such as a sodium salt, potassium salt, calcium salt, ammonium salt, ethanolamine salt, triethylamine salt, dicyclohexylamine salt and the like, and a salt with an amino acid such as an arginine salt, aspartic acid salt, glutamic acid salt, and the like.

Thus, the antimicrobial composition can be used in the form of a pharmaceutical preparation, for example, in solid, semisolid or liquid form, which contains an active compound of the invention in admixture with an organic or inorganic pharmaceutical carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The antimicrobial compositions can also contain preservative or bacteriostatic agents to keep the active ingredient in the desired preparations stable in activity. The active object compound is included in the antimicrobial composition in an amount sufficient to produce the desired therapeutic effect upon the process or condition caused by bacterial infection.

For applying this composition to humans, it is preferably to apply it by intravenous, intramuscular or oral administration. While the dosage or therapeutically effective amount of the object compound of this invention varies from and also depends upon the age and condition of each individual patient to be treated, a daily dose of about 2–100 mg. of the active ingredient/kg. of a human being or an animal is generally given for treating diseases, and an average single dose of about 50 mg., 100 mg., 250 mg. and 500 mg. is generally administered.

Example of Fermentation (1) Culture medium (100 ml) containing 2% of starch, 1% of cottonseed meal and 1% of dried yeast was poured into each of five 500 ml. Sakaguchi-flasks and sterilized at 120° C. for 20 minutes. A loopful of slant culture of *Streptomyces rubellomurinus* FERM receipt No. 3563 (ATCC No. 31215) was inoculated to each of the media and cultured at 30° C. for 2 days. The resultant culture was inoculated to a medium (20 l) containing 5% of soluble starch, 0.5% of cottonseed meal, 2.5% of gluten meal, 0.5% of dried yeast, 1% of $MgSO_4 \cdot 4H_2O$, 1% of $KH_2PO_4$ and 0.7% of $Na_2HPO_4 \cdot 12H_2O$ in a 30 l.Jar-fermentor which had been sterilized at 120° C. for 20 minutes in advance, and cultured at 30° C. for 3 days.

After the culture was completed, diatomaceous earth (400 g) was added to the culture broth and the mixture was filtered. The filtrate (20 l) was concentrated under reduced pressure to a volume of 1 liter. To the concentrate was added methanol (4 l), and the mixture was stirred to give a precipitate, the precipitate was removed by filtration and the filtrate was concentrated to a volume of 1 liter. The resultant concentrate was passed through a column of activated charcoal. The passed-through solution was adjusted to pH 2.0 with a cation exchange resin, Duolite C-20 (trade mark, made by Diamond Shamrock Chemical Co.) ($H^+$ type; 500 ml) and passed through a column of Duolite A6 (trade mark, made by Diamond Shamrock Chemical Co.) ($OH^-$ type) (500 ml). Subsequently, elution was carried out with 0.1N aqueous sodium hydroxide solution (1500 ml). The eluate was adjusted to pH 2.0 with Duolite C-20 ($H^+$ type) and then passed through a column of activated charcoal. The object compound was eluted with 70% aqueous acetone (1 l). Fractions containing the object compound were collected and concentrated under reduced pressure. The residue thus obtained, was adjusted to pH 6.5 with 6N aqueous sodium hydroxide solution and subjected to column chromatography on cellulose (300 ml) with an eluent (80% aqueous propanol). Fractions containing the object compound were collected and dried under reduced pressure to give a white powder (600 mg). The powder was dissolved in a small volume of methanol with heating, and then a small volume of acetone was added to the solution. The mixture was allowed to stand overnight at 4° C. to give crystals, which were filtered and dried to give monosodium salt of FR-900098 (300 mg) in the form of colorless crystals.

(2) Ten 500ml. Erlenmeyer flasks containing 100 ml of an aqueous medium containing 1% of potato starch, 1% of glycerol, 1% of cottonseed meal and 1% of dried yeast was sterilized at 120° C. for 20 minutes. To each of the flasks was inoculated a loopful of slant culture of *Streptomyces rubellomurinus* subsp. *indigoferus* ATCC 31304, whereafter the organism was grown on a rotary shaker at 30° C. for 3 days.

On the other hand, an aqueous medium (70 liters) containing 2% of soluble starch, 0.25% of corn steep liquor, 0.25% of dried yeast, 0.5% of cottonseed meal, 0.5% of wheat germ, 0.5% of $KH_2PO_4$, 0.5% of $Na_2HPO_4 \cdot 12H_2O$ and 0.000125% of $CoCl_2 \cdot 12H_2O$ was poured into a 100 liter jar-fermentor and sterilized at 120° C. for 30 minutes. To the medium was added the whole volume of the cultured broth, as obtained above and then the organism was grown at 30° C. for 3 days. During the culture period, the fermentation was conducted by stirring the broth with a propeller stirrer operating at 300 r.p.m., passing sterile air through the broth in a ratio of 70 liters/broth/minute and maintaining internal atmospheric pressure of the fermentor at 0.5 ($kg/cm^2$).

After completion of the culture, the cultured broth was adjusted to pH 2.8 with 6N hydrochloric acid to give a precipitate, which was removed by filtration. The filtrate was passed through a column of activated charcoal (10 liters). Then, elution was carried out with 70% aqueous acetone (20 liters). The eluate was concentrated under reduced pressure to give a residue, to which water was added to give an aqueous solution (15 liters). The aqueous solution was passed through a column of DEAE-Sephadex, ($H^+$) type (8 liters) (trade name, made by Pharmacia A.B.) which was previously treated with 1/100 M phosphate buffer solution (pH 6.0). Then, elution was carried out with 0.3 M aqueous sodium chloride solution (10 liters). The eluate was adjusted to pH 3.3 with 6N hydrochloric acid and then passed through a column of activated charcoal (2 liters). Water was added to the passed solution so that the total volume became 30 liters. The resultant aqueous solution was adjusted to pH 2.8 with 6N hydrochloric acid and then passed through a column of activated charcoal (7 liters). Then, elution was conducted with 70% aqueous acetone. The active fractions were collected, adjusted to pH 6.0 with 6N aqueous sodium hydroxide solution and concentrated under reduced pressure to a volume of 100 ml. The concentrate was subjected to column chromatography on cellulose. (1 liter). The column was developed with 75% aqueous propanol (2 liters) to give fraction (A) and then developed with 70% aqueous propanol (2 liters) to give fraction (B).

The fraction (A) was concentrated under reduced pressure to a volume of 40 ml and the resultant concentrate was passed through a column of Sephadex G-15 (1 liter) (trade name, made by Pharmacia A.B.) and then subjected to column chromatography on cellulose. The column was developed with 80% aqueous propanol. The active fractions were collected and concentrated under reduced pressure to give a residue, which was lyophilized to give the monosodium salt of FR-900098 (300 mg) as a white powder.

The fraction (B), as obtained above, was concentrated under reduced pressure to a volume of 60 ml and the resultant concentrate was passed through a column of Sephadex G-15 (1 liter) and then subjected to column chromatography on cellulose. The column was developed with 75% aqueous propanol. The active fractions were collected and evaporated to dryness to give a white powder of the monosodium salt of FR-33289 (600 mg).

Examples for the antimicrobial composition

[i] Preparation for injection

[1] The required quantities of sterile antibiotic, monosodium salt of FR-900098 were distributed into vials, each containing 500 mg. of the active ingredient. The vials were sealed hermetically to exclude bacteria. Whenever the vials are required for use, 2 ml. of sterile distilled water for injection is added to the vial and the vial is administered.

In substantially the same manner as described in the above example [1], there was prepared an injection preparation of an antibiotic as illustrated in the following Example [2].

[2] The monosodium salt of FR-33289 [500 mg.] was used as the active ingredient for injection.

[ii] Preparation of tablet

[1] A suitable formulation for a tablet consists of the following mixture.

| Monosodium salt of FR-33289 | 200 mg. |
| Mannitol | 400 mg. |
| Starch | 50 mg. |
| Magnesium stearate | 10 mg. |

[iii] Preparation of capsule

| Monopotassium salt of FR-900098 | 300 mg. |
| Magnesium stearate | 15 mg. |

The above ingredients were mixed and then inserted into a hard gelatin capsule in a conventional manner.

[iv] Preparation of oily suspension

| Monosodium salt of FR-900098 | 200 mg. |
| Lanette wax SX [trade name] | 50 mg. |
| Soft paraffin | 100 mg. |
| Brilliant blue FCF | 25 mg. |

The above ingredients were mixed with liquid paraffin so as to amount in total to 3 g. to give an infusion preparation.

We claim:

1. Antibiotic FR-900098 and the pharmaceutically acceptable salts thereof, having the following characteristics:
   (a) is effective in inhibiting the growth of various Gram-positive and Gram-negative bacteria; and as its monosodium salt,
   (b) has the following elemental analyses:
   C 27.74; H 5.03; N 6.66
   (and the others: phosphorus and oxgen);
   (c) has a melting point from 193° to 194° C. in the form of colorless prisms;
   (d) has an optical rotation $[\alpha]_D^{25} = 0$ (c = 1.0, in water);
   (e) has a characteristic infrared absorption spectrum as shown in the following, $\nu_{max}^{KBr}$ = 3450, 3400, 3350, 3100, 2930, 2800, 2420, 2320, 1615, 1570, 1495, 1450, 1420, 1370, 1310, 1280, 1240, 1220, 1200, 1180, 1160, 1090, 1080, 1050, 1040, 990, 980, 925, 910, 885, 810, 780, 760, 740, 710 cm$^{-1}$;
   (f) has a characteristic ultraviolet absorption spectrum as shown in the following, $\lambda_{max}^{H_2O}$ or $0.1NHCl$ = end absorption; $\lambda_{max}^{0.1N NaOH}$ = 230 nm (Shoulder) ($E_{1cm}^{1\%}$ = 325);
   (g) has a characteristic thin layer chromatography pattern as shown in the following,
   Stationary phase; Eastman Chromagram Sheet Cellulose No. 13254 (trade name, made by Eastman Kodak Co.)

| Developing solvent | Rf value |
| --- | --- |
| 75% Aqueous propanol | 0.5 |
| n-Butanol saturated with water | 0 |
| 70% Aqueous acetonitrile | 0.4 |

(h) is positive in color reaction with each of ferric chloride, potassium permanganate and iodine vapor, and is negative in color reaction by each of ninhydrin reaction and Molish's reaction; and
   (i) is very soluble in water and methanol, and is sparingly soluble in acetone and propanol, and is insoluble in ethyl acetate, chloroform and benzene.

2. Antiobiotic FR-33289, i.e., 3-(N-acetyl-N-hydroxyamino)-2-hydroxypropylphosphonic acid and the pharmaceutically acceptable salt thereof, having the following characteristics:
   (a) is effective in inhibiting the growth of various Gram-positive and Gram-negative bacteria; and as its monosodium salt,
   (b) has a characteristic infrared absorption spectrum as shown in the following,
   $\nu_{max}^{KBr}$ = 3300, 2900, 2400, 1740, 1620, 1420, 1240, 1140, 1040, 900 cm$^{-1}$;
   (c) has a characteristic nuclear magnetic resonance absorption spectrum as shown in the following, δ (ppm) in D$_2$O
   1.88 (2H, d.d. J = 6 and 18Hz),
   2.16 (3H, s),
   3.66 - 3.9 (2H, m),
   4.30 (1H, m)
   (d) has a characteristic thin layer chromatography pattern as shown in the following,
   Stationary phase; Eastman Chromagram Sheet Cellulose No. 13254 (trade name, made by Eastman Kodak Co.)

| Developing solvent | Rf |
|---|---|
| 60% Aqueous propanol | 0.6; and |

(e) is positive in color reaction with each of ferric chloride, potassium permanganate and iodine vapor.

3. The pharmaceutical acceptable salts of the antibiotic FR-900098, according to claim 1.

4. An alkali metal salt of the antibiotic FR-900098, according to claim 3.

5. The monosodium salt of the antibiotic FR-900098, according to claim 4.

6. A pharmaceutically acceptable salt of the antibiotic FR-33289, according to claim 2.

7. An alkali metal salt of the antibiotic FR-33289, according to claim 6.

8. The monosodium salt of the antibiotic FR-33289, according to claim 7.

9. An antimicrobial composition which comprises, as an effective ingredient, one or more compounds selected from the group consisting of antibiotics FR-900098 or the pharmaceutically acceptable salts thereof and FR-33289 or the pharmaceutically acceptable salts thereof and a non-toxic, pharmaceutically acceptable carrier.

UNITED STATES PATENT AND TRADEMARK OFFICE
CERTIFICATE OF CORRECTION

PATENT NO. : 4,143,135  Page 1 of 3
DATED : March 6, 1979
INVENTOR(S) : Yoshio Kuroda et al It is certified that error appears in the above-identified patent and that said Letters Patent are hereby corrected as shown below:

1. Column 2, line 30, delete ";" after the formula and insert --.--.

2. Column 2, line 40, delete "antibiolics" and insert --antibiotics--.

3. Column 2, line 43, delete "rebellomurinus" and insert --rubellomurinus--.

4. Column 4, line 30, after "production" and before "the" insert --of--.

5. Column 4, line 44, delete "melt" and insert --malt--.

6. Column 5, following line 50, to be included in the tabulation, insert -- D-Mannitol -
   D-Mannose -
   Salicin -

Note) ++ = Very good utilization
   + = Good utilization
   ± = Doubtful utilization
   - = No utilization  --.

UNITED STATES PATENT AND TRADEMARK OFFICE
CERTIFICATE OF CORRECTION

PATENT NO. : 4,143,135
DATED : March 6, 1979
INVENTOR(S) : Yoshio Kuroda et al

It is certified that error appears in the above-identified patent and that said Letters Patent are hereby corrected as shown below:

7. Column 7, in the table at the top of the column under the heading "Aerial Mycelium", delete "white gray, to very thin" and insert --white to gray, very thin--.

8. Column 8, line 32, "Streptomyces rebellomurinus" should be italicized.

9. Column 10, line 4 delete the formula:

$$\text{"CH}_3\text{CO-NCH}_2\text{CH}_2\text{CH}_2\overset{\overset{\text{OH}}{|}}{\underset{\underset{\text{OH}}{|}}{\text{P}}}\text{-OH"}$$

and insert the formula:

$$--\text{CH}_3\text{CO-NCH}_2\text{CH}_2\text{CH}_2\overset{\overset{\text{OH}}{|}}{\underset{\underset{\text{OH}}{|}}{\text{P}}}\text{-OH}$$

10. Column 10, line 7, delete "phosphonoic" and insert --phosphonic--.

11. Column 12, line 41, delete "projecting" and insert --protecting--.

UNITED STATES PATENT AND TRADEMARK OFFICE
CERTIFICATE OF CORRECTION

PATENT NO. : 4,143,135

DATED : March 6, 1979

INVENTOR(S) : Yoshio Kuroda et al

Page 3 of 3

It is certified that error appears in the above-identified patent and that said Letters Patent are hereby corrected as shown below:

12. Column 12, line 47, delete "net" and insert --not--.

13. Column 12, line 57, after "mice", insert --tested were--.

14. Column 16, lines 23 and 24, delete "$\lambda_{max}^{H_2O}$ or 0.1NHCl" and insert -- $\lambda_{max}^{H_2O}$ or 0.1NHCl --.

15. Column 16, line 24, delete "$\lambda_{max}^{0.1N\,NaOH}$" and insert -- $\lambda_{max}^{0.1N\,NaOH}$ --.

Signed and Sealed this

Twenty-second Day of January 1980

[SEAL]

Attest:

SIDNEY A. DIAMOND

Attesting Officer

Commissioner of Patents and Trademarks